United States Patent [19]

Brown

[11] 3,984,479
[45] Oct. 5, 1976

[54] PREPARATION OF 9-BBN
[75] Inventor: Herbert C. Brown, West Lafayette, Ind.
[73] Assignee: Aldrich-Boranes, Inc., Milwaukee, Wis.
[22] Filed: Nov. 8, 1973
[21] Appl. No.: 413,866

[52] U.S. Cl. .................................. 260/606.5 B
[51] Int. Cl.² ........................................ C07F 5/02
[58] Field of Search .......................... 260/606.5 B

[56] References Cited
UNITED STATES PATENTS

| | | | |
|---|---|---|---|
| 2,925,437 | 2/1960 | Brown | 260/606.5 B |
| 2,925,438 | 2/1960 | Brown | 260/606.5 B |
| 3,155,732 | 11/1964 | Lang et al. | 260/606.5 B |
| 3,157,704 | 11/1964 | Salgebarth | 260/606.5 B X |
| 3,180,894 | 4/1965 | Lang et al. | 260/606.5 B |

OTHER PUBLICATIONS

J.A.C.S v. 90 pp. 5280–5284 (1968).
J.A.C.S v. 81, pp. 6428–6437 (1959).
Chemistry & Industry, pp. 2087–2088 (1962).

Primary Examiner—Helen M. S. Sneed
Attorney, Agent, or Firm—Merriam, Marshall, Shapiro & Klose

[57] ABSTRACT

9-Borabicyclo (3.3.1) noname (9-BBN), a relatively stable solid dialkylborane, can be used to reduce a wide variety of reducible chemical compounds, including both organic and inorganic compounds. The stability of the reagent greatly reduces the operating difficulties encountered with other dialkylboranes having similar reduction properties, which are thermally and hydrolytically unstable.

3 Claims, No Drawings

PREPARATION OF 9-BBN

This invention relates to a novel method for the preparation of 9-borabicyclo[3.3.1]nonane and the use of this compound for the reduction of reducible chemical compounds.

It is known that diborane, $B_2H_6$, normally gaseous, is a compound which has an excellent ability to hydrogenate organic materials. The use of diborane for this purpose, however, is accompanied by many practical difficulties stemming from the highly reactive nature of the material. Diborane reacts explosively with air or oxygen and is hydrolytically unstable, reacting very rapidly with water to produce hydrogen. In addition, diborane is thermally unstable. Accordingly, the practical use of diborane in its gaseous state is accompanied with many problems which militate against its use.

Although diborane forms a stable complex with tetrahydrofuran (THF), this material is also subject to many of the disadvantages attending the use of gaseous diborane. The complex is similarly sensitive to the presence of water and oxygen and must be stored at low temperatures under an inert blanket in order to avoid loss of hydride activity.

Certain alkyl-substituted boranes, such as thexylborane and disiamylborane, are also known as excellent hydrogenating agents. These compounds, however, also suffer from many of the disadvantages of diborane, being thermally unstable and reacting spontaneously on exposure to air or water. These deficiencies similarly reduce to a large extent their usefulness as hydrogenating agents.

Certain borane derivatives, such as trimethylamineborane, are known to be thermally stable and resistant to the presence of oxygen and water. This stability, however, is obtained at the expense of the effectiveness of such compounds as hydrogenating agents. Other derivatives of borane, such as the alkali metal borohydrides, which are much more stable than is diborane, similarly possess poor hydrogenating properties. Thus, for example, sodium borohydride fails to reduce organic nitriles, whereas diborane reduces such nitriles rapidly. Another serious deficiency of the alkali metal borohydrides is that they are generally soluble only in the more polar solvents and cannot be used effectively in common inexpensive hydrocarbon solvents such as benzene, toluene or hexane.

In accordance with the invention, it has been found that 9-borabicyclo[3.3.1]nonane (hereinafter abbreviated as 9-BBN) possesses an unusual and unexpected combination of stability together with the power to hydrogenate a wide variety of organic and inorganic compounds. In another aspect of the invention, there is provided a process for the production of 9-BBN which avoids many of the operating difficulties encountered in the procedures used to prepare the compound in the past.

9-BBN is a known material, the use of which as a hydroborating agent has been described in the literature (JACS, 90, 5280–5283). It is a crystalline solid, m.p. 149–151° C., which possesses remarkable stability in air, being capable of being stored in a capped bottle without special precautions. It reacts with water only very slowly and can be distilled without degradation. In its relative stability, 9-BBN is very similar to compounds such as trimethylamineborane and the alkali metal borohydrides. Although the stability of 9-BBN in storage and handling was known (H. C. Brown, Boranes in Organic Chemistry, Cornell University Press (1972), p. 239), its properties appeared to indicate that like other relatively stable borane derivatives, 9-BBN would possess negligable reducing ability. Surprisingly, however, it is now been found that in solution 9-BBN is a remarkably powerful reducing agent, having the ability to reduce a wide variety of reducible compounds, both organic and inorganic.

In the practice of the invention, the material to be reduced is contacted with a solution of 9-BBN in an appropriate solvent, such as benzene, toluene, hexane, and similar hydrocarbon or other solvents, such as diglyme and tetrahydrofuran, which possess satisfactory solvent properties and are inert to the reactants. One or more molar equivalents of 9-BBN can be used per equivalent of the material to be reduced, depending on the nature of the functional group and the extent of hydrogenation which is desired.

In general, the reaction with 9-BBN leads to the formation of intermediate products which are then hydrolyzed with water, aqueous base, or aqueous acid, as appropriate, to obtain the desired reduction products.

The temperature of the reaction depends on the ease with which the compound being treated responds to hydrogenation. Relatively easily reduced compounds, such as aldehydes, can be hydrogenated almost instantly at room temperature, while others, such as esters, may require extended periods of reaction at the reflux temperature of the solvent. In general, any elevated temperature can be used which does not result in the decomposition of the individual reactants or desired products.

The process of the invention can be used for the hydrogenation of any compound having a reducible functional group containing an atom other than hydrogen and carbon. In certain instances, as in the case of inorganic compounds, the functional group may consist of a single element, such as sulfur, chlorine, bromine, iodine, silver, tin, iron or mercury, which is to be reduced to a lower valence state.

A particular group of reducible compounds with which the process of the invention is suitable includes those compounds containing a functional group in which an atom of oxygen, nitrogen, or sulfer is attached by multiple bonds to an atom of carbon, nitrogen, phosphorus, or oxygen. Typical examples of such compounds are those containing a carbonyl group (C=O), including aldehydes, ketones, carboxylic acids, quinones, amides, esters and lactones; nitriles (C≡N); nitro compounds (N=O); azo compounds (N=N); oximes (C=N) isocyanates (N=C); sulfones and sulfoxides (S=O); thioamides, thioketones and carbon disulfide (C=S); methylenephosphoranes (P=C); iminophosphoranes (P=N); iminosulfuranes (S=N); phosphine oxides (P=O); thiophosphates (P=S); oxygen (O=O) and ozone (O=O—O).

Another category of compounds which can be reduced by reaction with 9-BBN in accordance with the invention comprises organic compounds having a 3-membered ring in which one of the substituents is oxygen. Still another category of compounds which can be reduced in accordance with the invention includes inorganic compounds containing an atom which can exist in several valence states, such as stannic chloride, ferric chloride, and phosphorus pentachloride, whereby reaction with 9-BBN reduces the valence state of said atom.

The process of the invention is particularly useful for the hydrogenation of organic compounds containing a carbonyl group, e.g., aldehydes, ketones, carboxylic acids and derivatives of such acids. 9-BBN reacts almost instantaneously with such compounds, as exemplified by caproaldehyde, laurylaldehyde, benzaldehyde, 2-heptanone, 2-methylcyclohexanone, norcamphor, camphor, acetophenone, benzophenone, and cinnamaldehyde. Typical steroidal ketones are also readily reduced following the process of the invention, which is similarly effective for reducing alpha-haloaldehydes and ketones, such as phenacyl bromide, without loss of the halogen.

Fused ring structures containing a carbonyl group, such as anthraquinone, are readily reduced. For example, anthraquinone is readily reduced to the 9,10-dihydro-9,10-anthracenediol stage. The anthraquinone unit can have many substituents, such as 2-methylanthraquninone, 2-chloroanthraquinone, and the sodium salt of anthraquinone-2-sulfonic acid. Such treatment can be used advantageously to reduce many vat dyes to soluble form, which can then be reoxidized by air to the insoluble form.

The process of the invention is generally applicable to hydrogenation of carboxylic acids, as exemplified by caproic acid, stearic acid, pivalic acid, benzoic acid, cyclohexanecarboxylic acid, succinic acid, and phthalic acid, all of which are readily hydrogenated. In such hydrogenation, the carboxylic acids react readily with one molar equivalent of 9-BBN to liberate hydrogen and form the acyl derivative. A second mole of 9-BBN reacts slowly to produce an intermediate which on hydrolysis yields the aldehyde. A third mole of 9-BBN will react, preferably by heating to 100°C., hydrolysis of the product yielding the corresponding alcohol.

Derivatives of carboxylic acids, such as esters, lactones, salts, acid halides and amides are similarly readily hydrogenated following the process of the invention.

Although the hydrogenation of esters is slow at room temperature, the reaction proceeds rapidly at reflux temperature in a suitable solvent such as benzene or toluene. Examples of esters which can be hydrogenated in this manner are ethyl caproate, ethyl benzoate, phenyl acetate, and methyl stearate.

Lactones react with 9-BBN at a faster rate than do esters, the reaction proceeding satisfactorily at room temperature. Examples of lactones which can be hydrogenated include gamma-butyrolactone and phthalide. Primary amides such as caproamide and benzamide react with 9-BBN to liberate initially one mole of hydrogen. Further reaction with 9-BBN, which usually requires heating, yields an intermediate which on acid hydrolysis produces the corresponding amine. The hydrogenation of tertiary amides, such as N,N-dimethylcaproamide and N,N-dimethyl benzamide is considerably faster and proceeds rapidly to the amine stage. If the reaction is carried out using only one equivalent of the reagent (9-BBN) hydrolysis of the intermediate product yields the corresponding aldehyde.

Nitriles, such as capronitrile, lauronitrile and benzonitrile, react readily with one equivalent of 9-BBN to yield the aldehyde after hydrolysis. If the reaction is carried out with two equivalents of 9-BBN, the ultimate product is the amine. Similarly, both aliphatic and aromatic nitro compounds can be hydrogenated in accordance with the process of the invention by heating with a solution of 9-BBN in a solvent such as benzene, followed by hydrolysis. Hydrogenation of azobenzene is slow at room temperature but proceeds more rapidly at elevated temperatures. The reaction of azoxybenzene is much faster and proceeds at a reasonable rate at 25° C.

Oximes react with 9-BBN rapidly to liberate one mole of hydrogen. These compounds, such as cyclohexanone oxime, react with a second mole of reagent, preferably at elevated temperature, to produce the corresponding hydroxylamine after hydrolysis.

Isocyanates, such as phenylisocyanate, react with 9-BBN to consume two moles of reagent rapidly. Pyridine and pyridine-N-oxide react more slowly with 9-BBN and require elevated temperatures.

Sulfonic acids, such as methane sulfonic acid and toluene sulfonic acid, liberate hydrogen rapidly at room temperature, while further reduction requires heating at elevated temperatures. The reduction of sulfones also requires elevated temperatures, while sulfoxides are reduced at a more rapid rate at lower temperatures.

The process of the invention can also be applied to the reduction of inorganic materials. In general, compounds containing metal atoms or atoms such as sulfur and nitrogen, which can exist in several valence states, can be reduced to a form in which the multivalent atom is reduced to one of its lower valence states by treatment with 9-BBN in accordance with the invention. Thus, for example, carbon monoxide, nitric oxide, and sulfur dioxide react readily with 9-BBN. Treatment of stannic chloride, ferric chloride, or mercuric chloride results in rapid reduction to the lower valence state.

The process of the invention is suitable for the treatment of inorganic compounds containing ions of metals lower than hydrogen in the electromotive series, whereby the metal can be reduced to its free state. For example, salts and other inorganic compounds containing mercury, silver or platinum can be treated to produce the free metal. In some instances, particularly that of platinum, catalytically active forms of the metal can be made in this manner.

9-BBN reacts readily with organic compounds which contain a 3- membered ring structure including at least one oxygen atom, such as epoxides, to open the ring. Epoxides such as 1,2-butylene oxide, cyclohexane oxide, styrene oxide and 1-methylcyclohexane oxide react slowly at room temperature but readily at a temperature of 70° C. or above.

9-BBN is soluble in a wide variety of organic liquids, including the common hydrocarbon solvents such as hexane, cyclohexane, benzene, toluene, and xylene, and also in other organic liquids, such as ethyl ether, n-butylether, and tetrahydrofuran. Halogenated solvents, such as methylene chloride, ethylene dichloride, and chlorobenzene can be used, but are less desirable because of slow reaction with the reagent. This property permits the process of the invention to be applied advantageously to the treatment of such organic liquids for removal of minor amounts of impurities which may produce an objectionable color or odor. For example, the addition of 9-BBN to dialkylphthalates used as plasticizers will remove trace quantities of aldehydes which frequently impart undesirable colors to the plasticized polymers. Similarly, the addition of small quantities of the reagent to aromatic bases improves the color and stabilizes the material against air oxidation.

At times it may be more effective to add the 9-BBN to products containing small quantities of a strong base. The stability of 9-BBN to air permits the material to be readily handled in such applications while other reactive dialkylboranes cannot be used in this manner.

The following examples are presented to illustrate the process of the invention.

EXAMPLE 1

Reduction of Cyclohexanone

One liter of tetrahydrofuran is placed in a two liter flask flushed with nitrogen. One mole of cyclohexanone is added, and one mole of 9-BBN is then added in portions. The reactions mixture is stirred for one hour. Treatment with excess strong alkali such as aqueous NaOH gives a dry THF solution of cyclohexanol and an aqueous phase containing an ate complex of B-hydroxy-9-BBN. Separation of the non-aqueous solution and evaporation of the THF gives an essentially quantitative yield of cyclohexanol.

EXAMPLE 2

Reduction of 2-Methylcyclohexanone

Following the procedure of Example 1, one mole of 9-BBN is reacted with one mole of 2-methylcyclohexanone. The hydrogenated product, recovered in essentially quantitative yield, is predominately trans-2-methylcyclohexanol. By contrast, the reduction of this compound by other dialkylboranes, such as disiamylborane and diisopinocampheylborane, results in a product which is predominately the cis isomer.

EXAMPLE 3

Reduction of Lauric Acid

Following the procedure of Example 1, one mole of lauric acid is reacted with three moles of 9-BBN, added in increments. The reaction mixture is heated under reflux conditions for three hours. Following hydrolysis, an essentially quantitative yield of lauryl alcohol is obtained.

EXAMPLE 4

Reduction of 1,2-Butylene Oxide

In a two liter flask flushed with nitrogen was placed one liter of tetrahydrofuran, one mole of 1,2-butylene oxide and 7.5 mmol of lithium borohydride as a catalyst. One mole of 9-BBN was added in portions over a one-hour period, while cooling the flask to retain the temperature at approximately 25°C. The reaction was over in approximately the time required for the addition of the 9-BBN. Addition of one mole of ethanolamine precipitated a solid complex of B-hydroxy-9-BBN. Gas chromatographic examination of the solution revealed a 98% yield of butanols, consisting of 98% 2-butanol and 2% 1-butanol.

EXAMPLE 5

Reduction of Silver Bromide

In a one liter flask is placed 500 ml. of tetrahydrofuran, and 0.1 mole of silver bromide. To this is added 0.1 mole of 9-BBN. The mixture is stirred overnight. The product is finely divided silver.

EXAMPLE 6

Reduction of Chloroplatinic Acid

Chloroplatinic acid, 0.01 mole, is placed in 500 ml. of tetrahydrofuran. To this is added 0.05 mole of 9-BBN. There is a rapid reaction and finely divided platinum is precipitated. The precipitate is collected and washed with acid and water. The product is a highly active catalyst for the hydrogenation of unsaturated organic compounds.

Alternatively, the above reduction can be carried out in the presence of a high surface area support, such as carbon, alumina, and silica. In this way highly active catalysts on supports can be prepared.

The known methods for the production of 9-BBN have involved the use of diborane, a dialkylborane, or borane-THF complex, all of which are highly reactive and require special precautions during use. In another aspect of the present invention, there is provided a novel method for the preparation of 9-BBN which avoids the operating difficulties encountered in the known processes.

In the present method, sodium borohydride, a stable, easily handled material, is suspended in tetrahydrofuran (THF). Boron trifluoride, either in gaseous form or as the appropriate etherate, is added to generate borane, which forms a stable THF complex, with the precipitation of sodium fluoroborate. Without separation of the precipitated sodium fluoroborate, an equimolar amount (based on the borane) of 1,5-cyclooctadiene is added. The solution is then heated to reflux for approximately one hour and the hot solution is filtered to remove the precipitate of sodium fluoroborate which is present in the reaction mixture. On cooling, solid 9-BBN crystallizes out of the solution and is recovered by conventional means.

In addition to avoiding the handling of reactive borane materials, this process avoids the necessity for filtering any precipitates out of the reaction mixture at an intermediate stage in the process, which might lead to the loss of borane and the necessity for restandardizing the solution. In addition, the prior processes formed undesirable polymeric and other reaction byproducts all of which lead to poor yields of the desired 9-BBN. The novel process of the invention avoids all of these difficulties and permits the preparation of 9-BBN in a simple and efficient manner.

The preparation of 9-BBN is illustrated in the following example.

EXAMPLE 7

Preparation of 9-BBN

A 12 liter flask equipped with a thermometer well, gas inlet tube, addition funnel, mechanical stirrer and reflux condenser is heated while flushing with nitrogen. Sodium borohydride (360g.) is added, followed by 9 liters of dried tetrahydrofuran. Boron trifluoride gas (814g.) is then added with stirring and external cooling at a rate such that temperature does not exceed 10°C. When the boron trifluoride addition is complete, the reaction mixture is stirred for an additional 0.5 hour. There is then added to the reaction mixture, 1,5-cyclooctadiene (1483 ml) with stirring and external cooling at a rate such that the temperature does not exceed 10°C. After standing overnight at 20°–25°C. the reaction mixture is stirred for one hour at 20°–25°C., after which the mixture is heated to reflux and maintained at reflux for one hour. The hot reaction mixture is then pressure filtered through an external glass filter and washed once with one liter of hot THF to give approximately 10 liters of a crystal clear and colorless solution of 9-BBN in THF. Upon cooling overnight at 20°–25°C., a large mass of pure white crystals settles out. Cooling at 0°–5°C. for 24 hours completes the crystallization. The mother liquor is removed from the crystals under positive nitrogen pressure. A total of 7.25 liters of liquid is collected containing about 3.2 moles of dissolved 9-BBN as measured by active hydride analysis. The solid crystalline 9-BBN is vacuum dried under a nitrogen atmosphere to give 996g. (66% yield) of a finely divided, while crystalline, free flowing powder, m.p. 152°–153°C. The solid 9-BBN prepared in this manner is not pyrophoric.

The foregoing detailed description has been given for clearness of understanding only, and no unnecessary limitations should be understood therefrom, as modifications will be obvious to those skilled in the art.

I claim:

1. A process for the preparation of 9-borabicyclo nonane comprising suspending sodium borohydride in tetrahydrofuran, adding $BF_3$ to the suspension to generate in situ a borane-tetrahydrofuran complex with the precipitation of sodium fluoroborate, adding 1,5-cyclooctadiene to thereaction mixture without the separation of the precipitated sodium fluoroborate while maintaining a temperature below about 10° C, heating the reaction mixture and separating a hot liquid phase containing dissolved 9-borabicyclo nonane from the solid sodium fluoroborate.

2. A process in accordance with claim 1 which includes the additional step of recovering 9-borabicyclo nonane as a solid product from said liquid phase.

3. The process of claim 2 in which solid 9-borabicyclo nonane is recovered by cooling said liquid phase to cause crystallization of solid 9-borabicyclo nonane and separating said solid from the residual liquid.

* * * * *

UNITED STATES PATENT AND TRADEMARK OFFICE
CERTIFICATE OF CORRECTION

PATENT NO. : 3,984,479
DATED : October 5, 1976
INVENTOR(S) : Herbert V. Brown

It is certified that error appears in the above–identified patent and that said Letters Patent are hereby corrected as shown below:

Col. 8, claim 1, line 1, change "9-borabicyclo nonane" to --9-borabicyclo[3.3.1]nonane--.

Col. 8, claim 1, line 7, change "thereaction" to --the reaction--.

Col. 8, claim 1, line 11, change "9-borabicyclo nonane" to --9-borabicyclo[3.3.1]nonane--.

Col. 8, claim 2, line 14, change "9-borabicyclo nonane" to --9-borabicyclo[3.3.1]nonane--.

Col. 8, claim 3, line 16, change "9-borabicyclo nonane" to --9-borabicyclo[3.3.1]nonane--.

Col. 8, claim 3, line 18, change "9-borabicyclo nonane" to --9-borabicyclo[3.3.1]nonane--.

Signed and Sealed this

Fourth Day of January 1977

[SEAL]

Attest:

RUTH C. MASON
Attesting Officer

C. MARSHALL DANN
Commissioner of Patents and Trademarks